US008965528B2

United States Patent
Howard

(10) Patent No.: US 8,965,528 B2
(45) Date of Patent: Feb. 24, 2015

(54) SYSTEMS AND METHODS FOR MAKING AND USING ELECTRICAL STIMULATION LEADS WITH SHAPED MESH CONTACT ASSEMBLIES

(71) Applicant: Boston Scientific Neuromodulation Corporation, Valencia, CA (US)

(72) Inventor: Joshua Dale Howard, Chatsworth, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 0 days.

(21) Appl. No.: 14/080,424

(22) Filed: Nov. 14, 2013

(65) Prior Publication Data

US 2014/0155967 A1   Jun. 5, 2014

Related U.S. Application Data

(60) Provisional application No. 61/732,779, filed on Dec. 3, 2012.

(51) Int. Cl.
*A61N 1/00* (2006.01)
*A61N 1/05* (2006.01)
*H01R 24/58* (2011.01)
*H01R 107/00* (2006.01)

(52) U.S. Cl.
CPC ............... *A61N 1/05* (2013.01); *A61N 1/0551* (2013.01); *H01R 24/58* (2013.01); *A61B 2562/225* (2013.01); *H01R 2201/12* (2013.01); *H01R 2107/00* (2013.01)
USPC ............................................ 607/116; 607/37

(58) Field of Classification Search
USPC ................................................. 607/37, 116
See application file for complete search history.

(56) References Cited

U.S. PATENT DOCUMENTS

| 6,181,969 | B1 | 1/2001 | Gord |
| 6,516,227 | B1 | 2/2003 | Meadows et al. |
| 6,609,029 | B1 | 8/2003 | Mann et al. |
| 6,609,032 | B1 | 8/2003 | Woods et al. |
| 6,741,892 | B1 | 5/2004 | Meadows et al. |
| 7,244,150 | B1 | 7/2007 | Brase et al. |
| 7,437,193 | B2 | 10/2008 | Parramon et al. |
| 7,672,734 | B2 | 3/2010 | Anderson et al. |
| 7,761,165 | B1 | 7/2010 | He et al. |
| 7,949,395 | B2 | 5/2011 | Kuzma |
| 7,974,706 | B2 | 7/2011 | Moffitt et al. |
| 8,175,710 | B2 | 5/2012 | He |
| 8,224,450 | B2 | 7/2012 | Brase |
| 8,364,278 | B2 | 1/2013 | Pianca et al. |
| 2005/0131481 | A1* | 6/2005 | Ries et al. ............... 607/36 |
| 2007/0150036 | A1 | 6/2007 | Anderson |

* cited by examiner

Primary Examiner — Nicole F Lavert
(74) Attorney, Agent, or Firm — Lowe Graham Jones PLLC; Bruce E. Black

(57) ABSTRACT

An electrical stimulation lead includes a lead body with electrodes disposed along the distal end portion of the lead body and terminals disposed along the proximal end portion of the lead body. Conductors electrically couple the terminals to the electrodes. A contact assembly is disposed at one of the proximal end portion or the distal end portion of the lead body. The contact assembly is formed from a shaped mesh and includes annular grooves defined along an outer surface of the shaped mesh; and a stylet tube disposed in a contact assembly lumen. Each of the conductors extends along at least a portion of the shaped mesh within the contact assembly lumen and external to the stylet tube. For each of the annular grooves, one of the electrodes or one of the terminals is disposed in the annular groove.

20 Claims, 9 Drawing Sheets

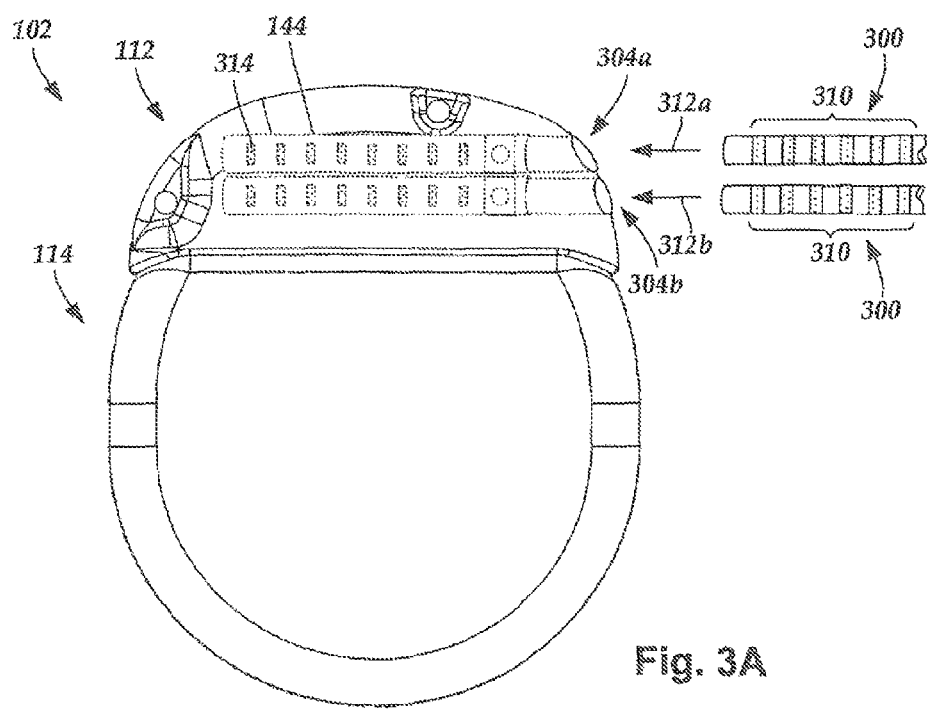

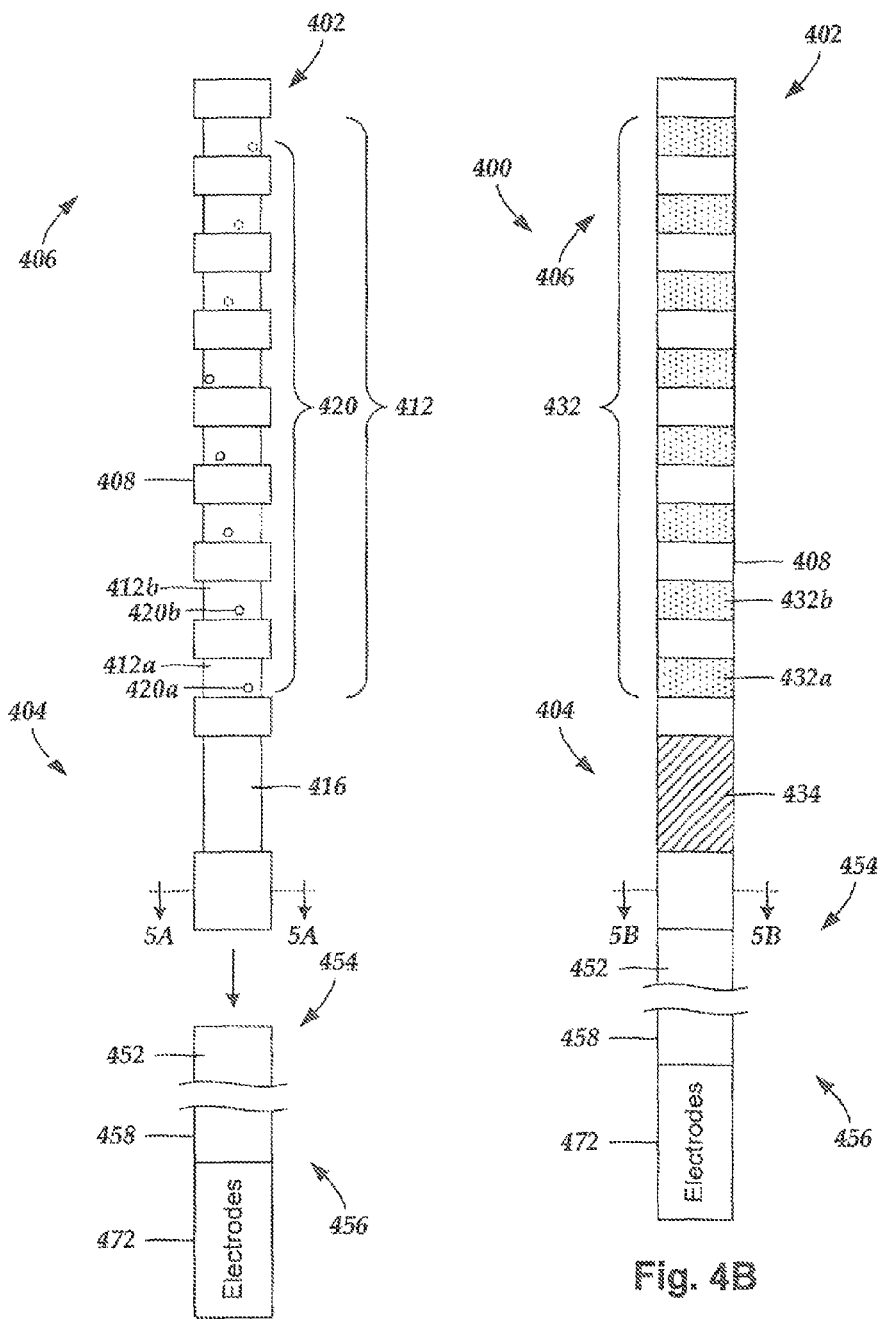

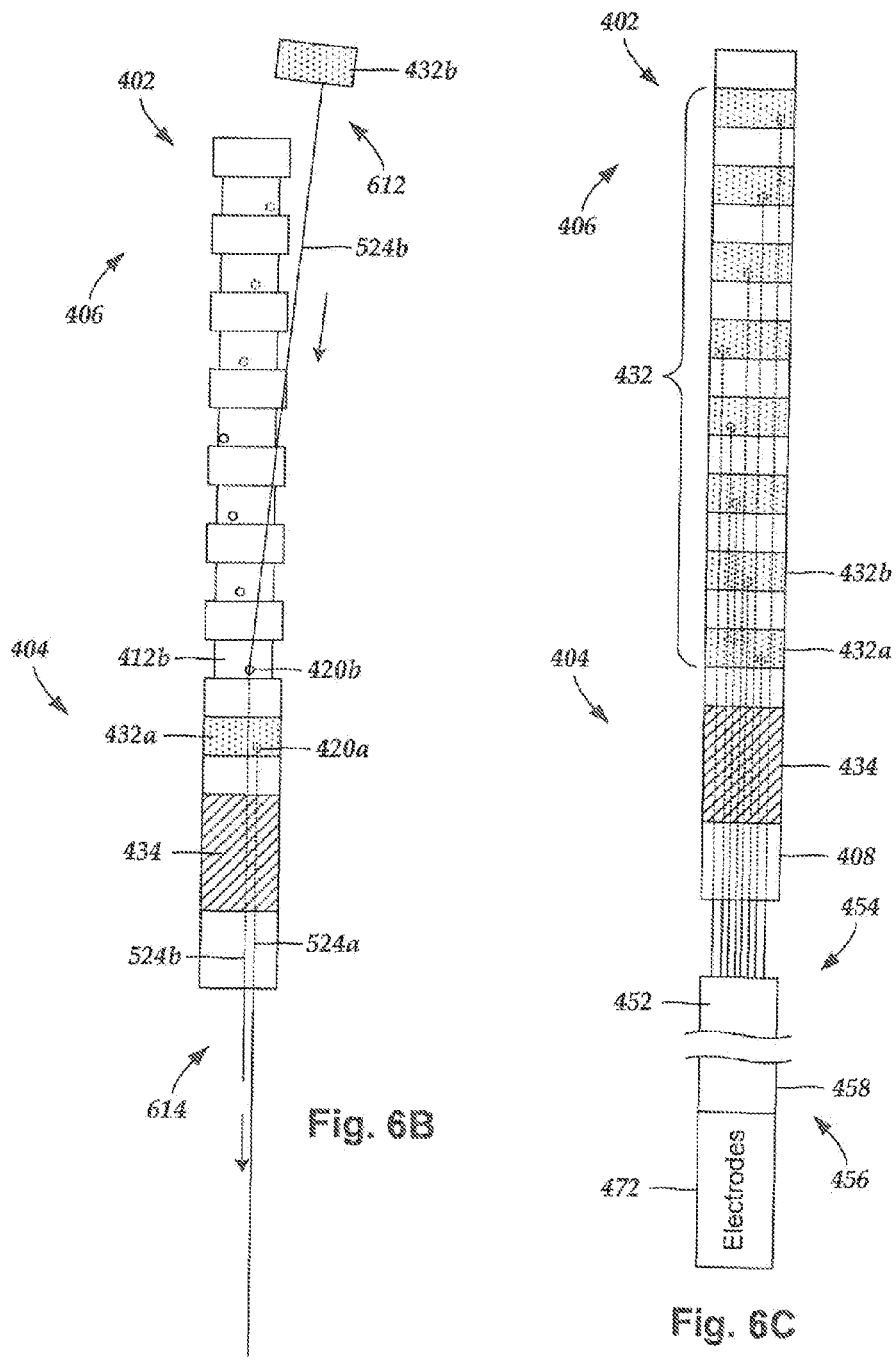

SYSTEMS AND METHODS FOR MAKING AND USING ELECTRICAL STIMULATION LEADS WITH SHAPED MESH CONTACT ASSEMBLIES

CROSS-REFERENCE TO RELATED APPLICATIONS

This application claims the benefit under 35 U.S.C. §119 (e) of U.S. Provisional Patent Application Ser. No. 61/732,779 filed Dec. 3, 2012, which is incorporated herein by reference.

FIELD

The present invention is directed to the area of implantable electrical stimulation systems and methods of making and using the systems. The present invention is also directed implantable electrical stimulation leads having contact assemblies formed from shaped mesh, as well as methods of making and using the leads, contact assemblies, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, an electrical stimulation lead includes a lead body having a distal end portion, a proximal end portion, and a longitudinal length. A plurality of electrodes is disposed along the distal end portion of the lead body. A plurality of terminals is disposed along the proximal end portion of the lead body. A plurality of conductors electrically couples each of the plurality of terminals to at least one of the plurality of electrodes. A contact assembly is disposed at one of the proximal end portion or the distal end portion of the lead body. The contact assembly is formed from a shaped mesh. The shaped mesh has an outer surface and defines a contact assembly lumen. The shaped mesh includes a plurality of annular grooves defined along the outer surface of the shaped mesh; and a stylet tube disposed in the contact assembly lumen. The stylet tube defines a stylet lumen. Each of the plurality of conductors extends along at least a portion of the shaped mesh within the contact assembly lumen and external to the stylet tube. For each annular groove of the plurality of annular grooves, one of the plurality of electrodes or one of the plurality of terminals is disposed in the annular groove.

In another embodiment, a method of forming an electrical stimulation lead includes providing a contact assembly formed from a shaped mesh. The contact assembly has a first end portion, a second end portion, a longitudinal length, and an outer surface. The contact assembly includes a plurality of annular grooves defined along the outer surface of the shaped mesh. The plurality of annular grooves includes a first annular groove and a second annular groove. A first conductor aperture is defined within the first annular groove and a second conductor aperture is defined within the second annular groove. A first end portion of an elongated first conductor is coupled to a first contact. A second end portion of the first conductor is extended through the first conductor aperture of the contact assembly. The first contact is disposed within the first annular groove. The second end portion of the first conductor is extended out of the first end portion of the contact assembly. The second end portion of the first conductor is extended into a first end portion of a lead body. The second end portion of the first conductor is coupled to a second contact disposed along a second end portion of the lead body. The first end portion of the lead body is coupled to the first end portion of the contact assembly.

In yet another embodiment, a method of forming an electrical stimulation lead includes providing a contact assembly. The contact assembly has a first end portion, a second end portion, a longitudinal length, and an outer surface. The contact assembly includes a plurality of annular grooves defined along the outer surface of the contact assembly. The plurality of annular grooves includes a first annular groove and a second annular groove. A first conductor aperture is defined within the first annular groove. A second conductor aperture is defined within the second annular groove. A first end portion of an elongated first conductor is coupled to a first contact. A second end portion of the first conductor is extended through the first conductor aperture of the contact assembly. The first contact is disposed within the first annular groove. The second end portion of the first conductor is extended out of the first end portion of the contact assembly. The second end portion of the first conductor is extended into a first end portion of a lead body. The second end portion of the first conductor is coupled to a second contact disposed along a second end portion of the lead body. The first end portion of the lead body is coupled to the first end portion of the contact assembly.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 3A is a schematic side view of one embodiment of the control module of FIG. 1 configured and arranged to electrically couple to an elongated device, according to the invention;

FIG. 4A is a schematic side view of one embodiment of a contact assembly configured and arranged for coupling to a proximal end of a lead body, according to the invention;

FIG. 4B is a schematic side view of one embodiment of a lead that includes the contact assembly of FIG. 4A, where terminals are disposed on the contact assembly and the contact assembly is coupled to a proximal end of the lead body of FIG. 4A, according to the invention;

FIG. 6B is a schematic side view of one embodiment of the retention sleeve and the first terminal of FIG. 6A coupled to the contact assembly of FIG. 6A, and where one end of a second conductor is coupled to a second terminal and an opposing end of the second conductor is extended into a second conductor aperture defined in the contact assembly and out a first end portion of the contact assembly, according to the invention;

FIG. 6C is a schematic side view of one embodiment of the contact assembly of FIG. 4A and the lead body of FIG. 4A, where a plurality of terminals are coupled to the contact assembly, and where a plurality of conductors couple the plurality of terminals to the lead body, according the invention;

DETAILED DESCRIPTION

The present invention is directed to the area of implantable electrical stimulation systems and methods of making and using the systems. The present invention is also directed implantable electrical stimulation leads having contact assemblies formed from shaped mesh, as well as methods of making and using the leads, contact assemblies, and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

Figure 1:
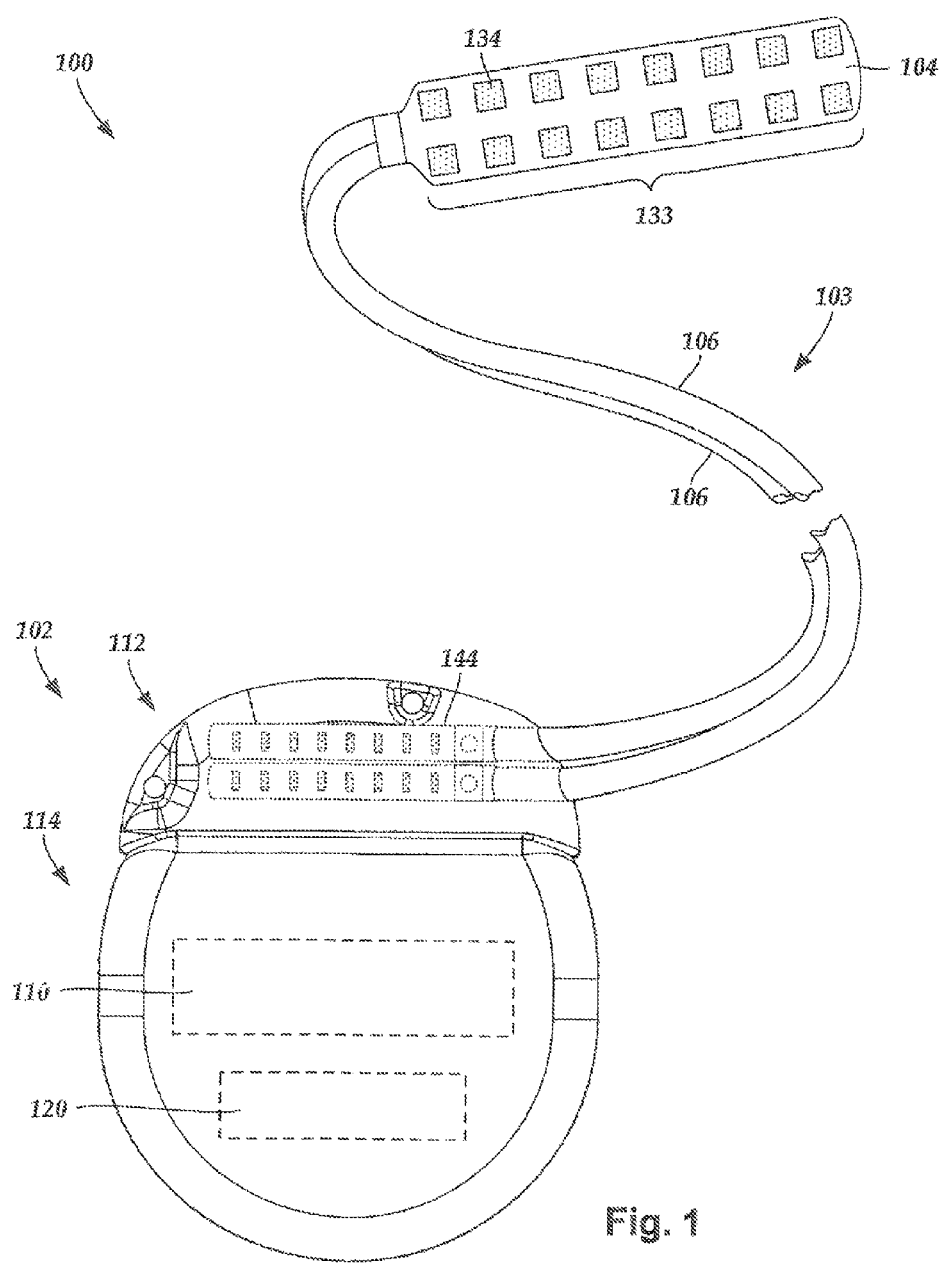
FIG. 1 is a schematic side view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array of electrodes 133, such as electrode 134, is disposed on the paddle body 104, and an array of terminals (e.g., 210 in FIG. 2A-2B) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
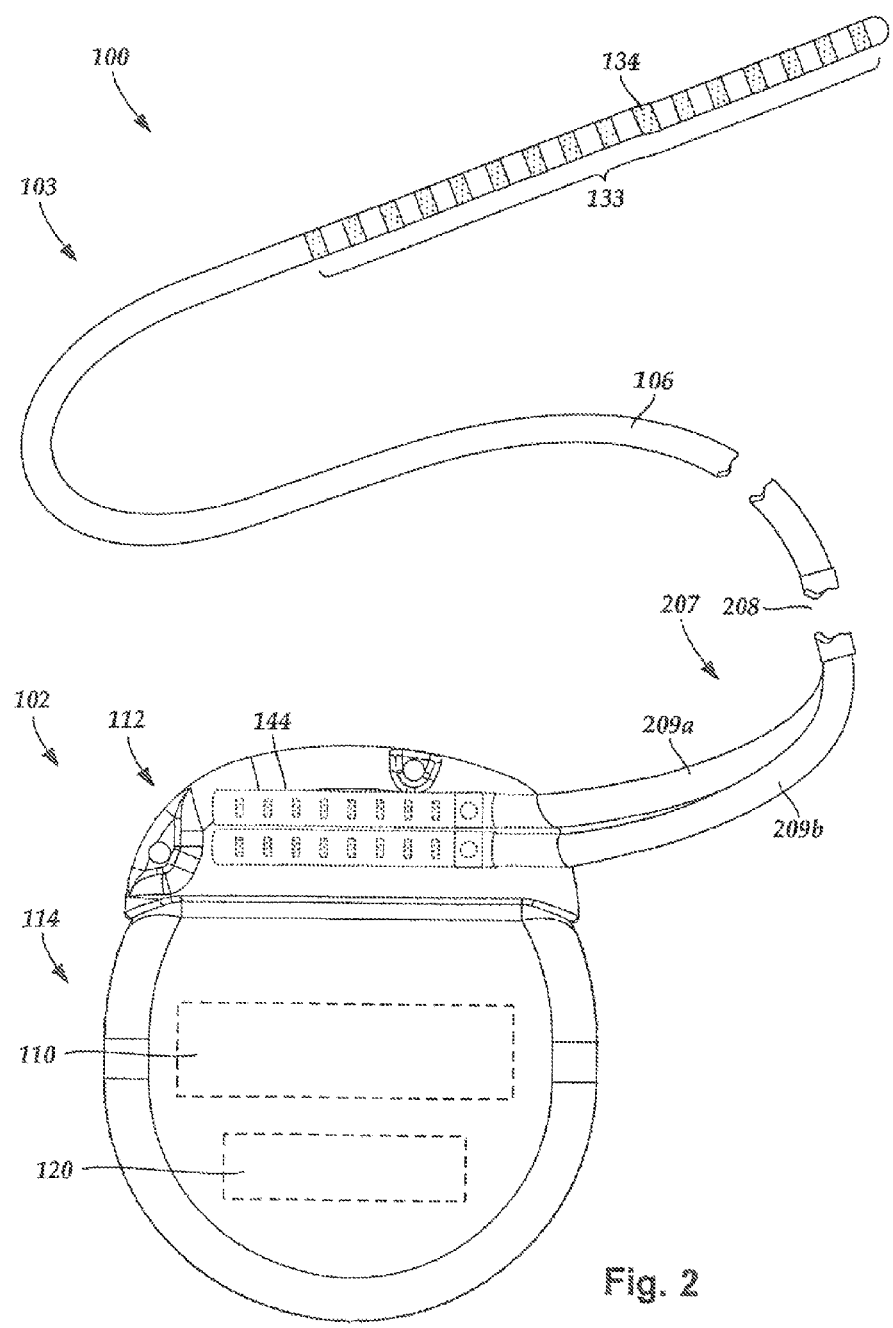
FIG. 2 is a schematic side view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (300 in FIGS. 3A-3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 207 configured and arranged for facilitating coupling of the lead 103 to the control module 102. The splitter 207 includes a splitter connector 208 configured to couple to a proximal end of the lead 103, and one or more splitter tails 209a and 209b configured and arranged to couple to the control module 102 (or another splitter, a lead extension, an adaptor, or the like).

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3B:
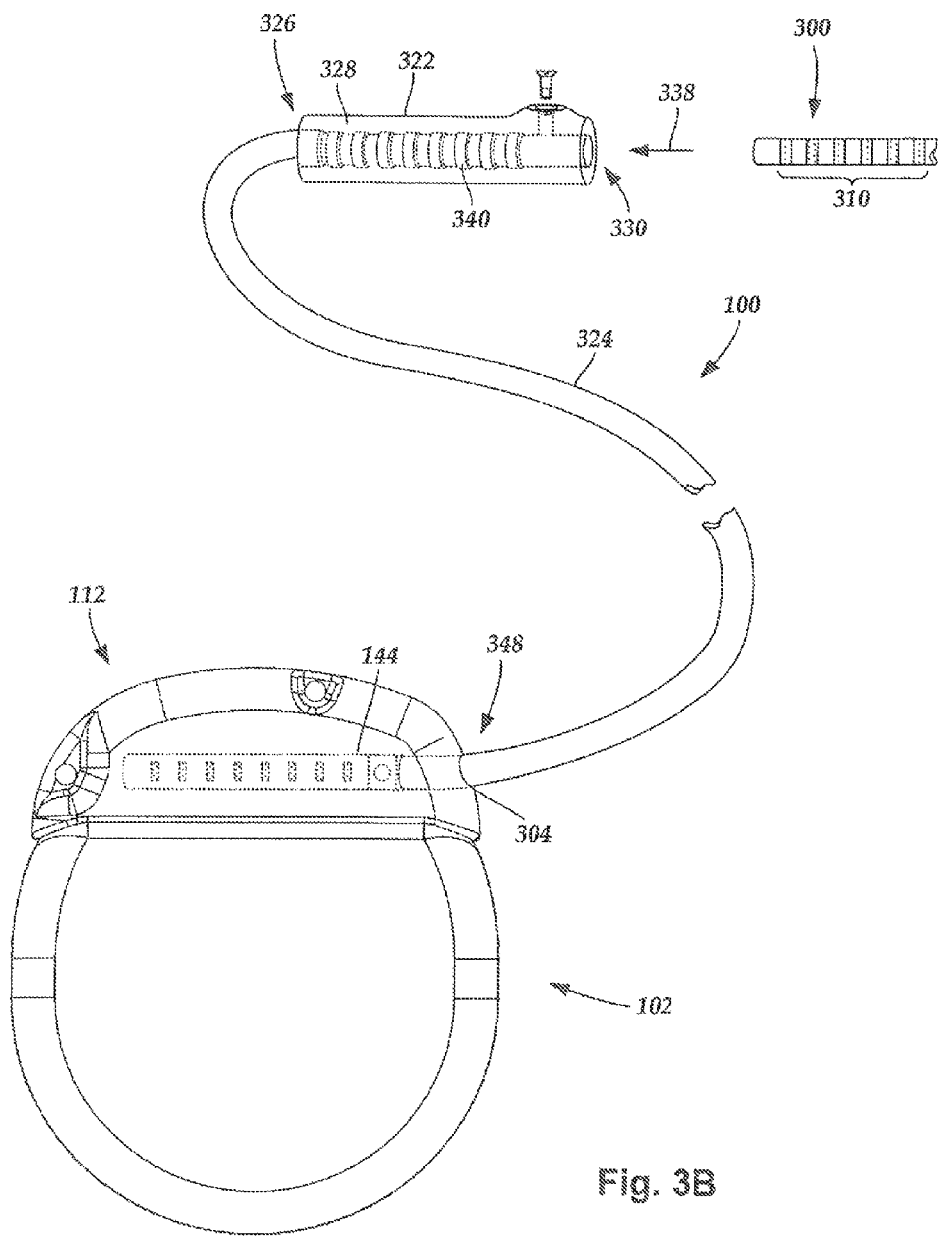
FIG. 3B is a schematic side view of one embodiment of a lead extension configured and arranged to electrically couple the elongated device of FIG. 2 to the control module of FIG. 1, according to the invention.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIGS. 3A-3B). The connector contacts are disposed in connectors (e.g., 144 in FIGS. 1-3B; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312a and 312b. In FIG. 3A (and in other figures), the connector housing 112 is shown having two ports 304a and 304b. The connector housing 112 can define any suitable number of ports including, for example, one, two, three, four, five, six, seven, eight, or more ports.

The control module connector 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 207 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contact 340. When the elongated device 300 is inserted into the port 330, the connector contacts 240 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically-conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

Turning to FIG. 4A, at least some conventional leads form contact assemblies by sliding contacts (e.g., terminals and electrodes) onto end portions of the lead body with electrically-nonconductive spacers disposed between adjacent contacts. Forming such contact assemblies may be labor-intensive and provide inconsistent pitches between adjacent contacts. Additionally, forming leads using such techniques may involve blind welding lead conductors to the contacts. Blind welding conductors to contacts may, likewise, be labor-intensive. Moreover, blind welding may produce inconsistent electrical connections.

As herein described, a contact assembly includes spaced-apart annular grooves configured to receive contacts. In at least some embodiments, the contact assembly is formed from mesh. It may be advantageous to use a mesh to facilitate disposing of the contacts into the annular grooves. For example, ring-shaped contacts may be slid into position along the contact assembly by squeezing the contact assembly through a bore of the contact while sliding the contact over the contact assembly. Additionally, using mesh may also be advantageous in that, once the contacts are disposed on the contact assembly, a stiffener may be added to the mesh to stiffen the mesh enough to enable insertion and removal of the contact assembly from a connector (e.g., of a control module, lead extension, adaptor, or the like).

FIGS. 4A-6C provide one embodiment of forming an enhanced contact assembly 402. The enhanced contact assembly 402 illustrated in FIGS. 4A-6C is formed along a proximal end portion of a lead. FIGS. 7A-7B provide another embodiment of forming an enhanced contact assembly 702 along a distal end portion of a lead. It will be understood that the enhanced contact assembly disclosed herein can be formed, for example, along either (or both) a distal end portion or a proximal end portion of a percutaneous lead. Additionally, the enhanced contact assembly may be disposed, for example, along a proximal end portion of a paddle lead.

FIG. 4A is a schematic side view of an embodiment of a contact assembly 402 and a lead body 452 having a proximal end portion 454 and an opposing distal end portion 456. Electrodes 472 are disposed along the distal end portion 456 of the lead body 452. The contact assembly 402 is configured and arranged for coupling to the proximal end portion 454 of the lead body 452. FIG. 4B is a schematic side view of an embodiment of a portion of a lead 400. The lead 400 includes the contact assembly 402 coupled to the proximal end portion 454 of the lead body 452.

As shown in FIG. 4B, in some embodiments the contact assembly 402 is disposed along the proximal end portion 454 of the lead body 452. The contact assembly 402 can be coupled to the lead body 452 in any suitable manner including, for example, adhesives, re-flowing, or the like. The lead body 452 has an outer surface 458. The contact assembly 402, likewise, has an outer surface 408. In at least some embodiments, the outer surface 458 of the lead body 452 is isodiametric with the outer surface 408 of the contact assembly 402.

As shown in FIG. 4A, multiple annular grooves 412 are defined along the outer surface 408 of the contact assembly 402. The annular grooves 412 are spaced-apart from one another along a longitudinal length of the contact assembly 402 and include a first annular groove 412a and a second annular groove 412b. As shown in FIG. 4B, the annular grooves 412 are configured to receive contacts, such as terminals 432. As shown in FIGS. 4A-4B, the spacing between adjacent annular grooves 412 determines the spacing between adjacent contacts, such as adjacent terminals 432. The contacts may be formed from any suitable shape including, for example, ring-shaped, C-shaped, segmented, or the like. As shown in FIGS. 4A-4B, the first groove 412a is configured to receive a first terminal 432a, whereas the second groove 412b receives a second terminal 432b.

In FIGS. 4A-4B (and in other figures), the contact assembly 402 is shown defining eight annular grooves 412. It is understood, however, that any suitable number of grooves can be defined along the outer surface 408 of the contact assembly 402 including one, two, three, four, five, six, seven, eight, nine, ten, eleven, twelve, fourteen, sixteen, twenty-four, thirty-two, or more annular grooves 412. The annular grooves 412 can have any suitable width or depth. In at least some embodiments, each of the annular grooves 412 is configured and arranged to receive a single contact.

In at least some embodiments, at least one conductor aperture 420 is defined in each of the annular grooves 412. For example, FIG. 4A shows a first conductor aperture 420a defined within the first annular groove 412a, and a second conductor aperture 420b defined within the second annular groove 412b. The conductor apertures 420 are defined along the outer surface 408 of the contact assembly 402 and extend to an interior of the contact assembly 402, as discussed in more detail with reference to FIGS. 5A-5B.

In at least some embodiments, each of the annular grooves 412 includes a single conductor aperture 420. It will be understood, however, that there can be any suitable number of conductor apertures 420 in the annular grooves 412 including, for example, one, two, three, four, five, six, seven, eight, or more conductor apertures 420. The apertures 420 may be of any suitable size or shape for receiving a conductor. The conductor apertures 420 can be formed in any suitable manner including, for example drilling, punching, laser cutting, or the like.

In the illustrated embodiments, the contact assembly 402 is formed from a mesh. The mesh of the contact assembly 402 can be formed from any non-conductive biocompatible material suitable for implantation including, for example, one or more polyesters, nylons, or the like. In at least some embodiments, the contact assembly 402 is formed from polyethylene terephthalate. In at least some embodiments, the contact assembly 402 can include one or more materials that are, for example, braided, coiled, woven, and the like or combinations thereof.

As shown in FIGS. 4A-4B, the contact assembly 402 may, optionally, define a retention sleeve annular groove 416 configured to receive a retention sleeve, such as retention sleeve 434. It may be advantageous to include the retention sleeve 434 in the contact assembly 402 to facilitate retention of the lead 400 within a connector. The retention sleeve 434 is used to secure a contact element, such as a set screw (not shown), to the retention sleeve 434. When the set screw is screwed, for example, through a wall of the connector, the end of the set screw may make contact with the retention sleeve 434 and provide mechanical locking, which prevents the proximal end 454 of the lead body 452 from being removed. In some embodiments, the retention sleeve 434 includes an optional radiopaque marker (not shown) located at the distal portion 456 of the lead body 452. As shown, the retention sleeve 434 is a cylindrical ring element, which may be made of a non-corrosive metal such as titanium, stainless steel, platinum/iridium alloy, and the like.

Figure 5A:
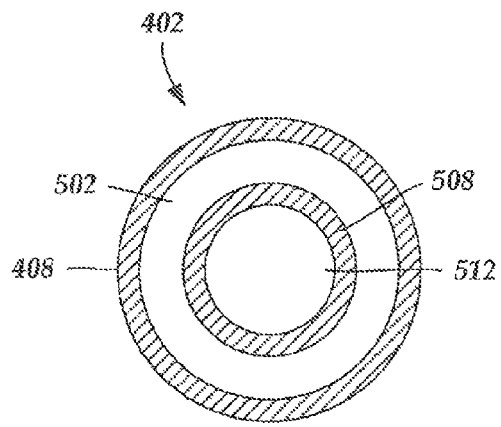
FIG. 5A is a schematic transverse cross-sectional view of one embodiment of the contact assembly of FIG. 4A, according to the invention.

FIG. 5A is a schematic transverse cross-sectional view of one embodiment of a portion of the contact assembly 402. The contact assembly 402 includes the outer surface 408 and defines a contact assembly lumen 502. In at least some embodiments, a stylet tube 508 is disposed in the contact assembly lumen 502. The contact assembly lumen 502 opens to the first end portion 404 of the contact assembly 402. The contact assembly lumen 502 can have any suitable shape (e.g., round, oval, or the like). The stylet tube 508 defines a stylet lumen 512 that is configured and arranged for receiving a stylet or guiding the lead 400 during implantation.

Figure 5B:
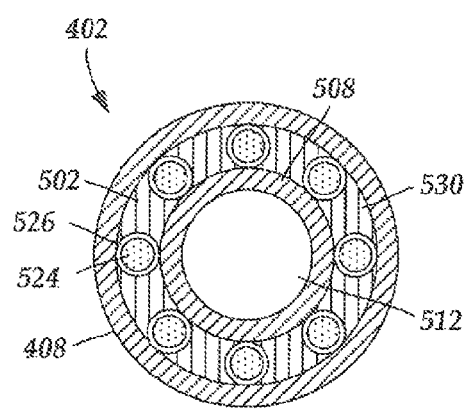
FIG. 5B is a schematic transverse cross-sectional view of one embodiment of the contact assembly of FIG. 4B, according to the invention.

FIG. 5B is a schematic transverse cross-sectional view of one embodiment of the contact assembly 402 with conductors 524 disposed in the contact assembly lumen 502. As shown in FIG. 5B, the conductors 524 extend along at least a portion of the contact assembly 402 within the assembly lumen 502 and external to the stylet tube 508. In at least some embodiments, electrically-nonconductive insulation 526 is disposed over each conductor 524 to electrically isolate each of the conductors from one another.

In at least some embodiments, a stiffening agent 530, such as epoxy, is backfilled into the contact assembly lumen 502 external to the stylet tube 508. It may be advantageous to apply a stiffening agent in the contact assembly lumen 502 to stiffen the contact assembly 402 and to prevent the conductors 524 from moving relative to one another and potentially rubbing off insulation. In at least some embodiments, the stiffening agent 530 is infused into the mesh of the contact assembly 402 to form a matrix. As explained in more detail below, it may be advantageous to apply the stiffening agent 530 after the contacts are disposed on the contact assembly 402.

Figure 6A:
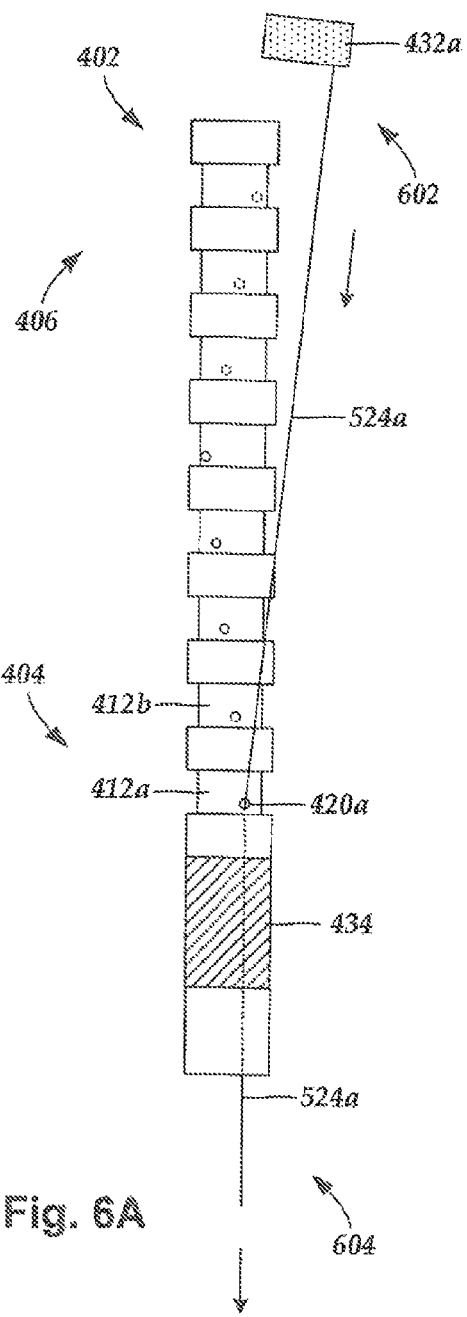
FIG. 6A is a schematic side view of the contact assembly of FIG. 4A, where a retention sleeve is disposed on the contact assembly, and where one end of a first conductor is coupled to a first terminal and an opposing end of the first conductor is extended into a first conductor aperture defined in the contact assembly and out a first end portion of the contact assembly, according to the invention.
Figures 7A, 7B:
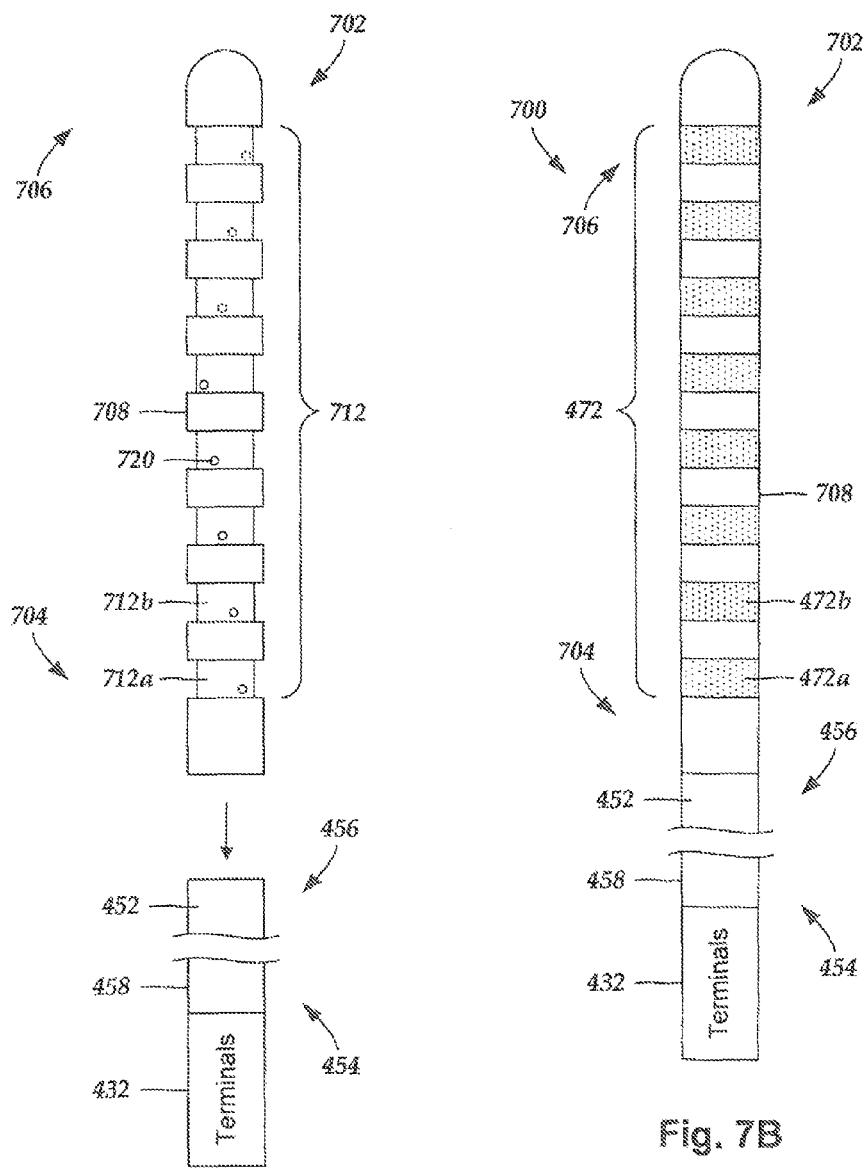
FIG. 7A is a schematic side view of another embodiment of a contact assembly configured and arranged for coupling to a distal end of a lead body, according to the invention.
FIG. 7B is a schematic side view of one embodiment of a lead that includes the contact assembly of FIG. 7A, where electrodes are disposed on the contact assembly and the contact assembly is coupled to a distal end of the lead body of FIG. 7A, according to the invention.

FIGS. 6A-6C illustrate one embodiment of: coupling contacts to conductors; disposing the contacts on the contact assembly by sliding the contacts over the second end portion of the contact assembly and into one of the annular grooves; and extending the conductors through the conductor apertures and into the contact assembly lumen. FIG. 6A is a schematic side view of the contact assembly 402. In the embodiment shown in FIG. 6A, the retention sleeve 434 is disposed in contact assembly 402 and the first terminal 432a is in the process of being disposed on the contact assembly 402. As shown in FIG. 6A, a first end 602 of a first conductor 524a is coupled to the first terminal 432a and an opposing end 604 of the first conductor 524a is extended into the first conductor aperture 420a defined in the first annular groove 412a of the contact assembly 402.

Coupling of the elongated conductor 524a to the contacts can be provided by any connecting method such as welding, or the like. Other suitable mechanisms to couple the two components may include, but not limited to, adhesives, crimping, or the like.

The contact can be of C-shaped or ring-shaped. The second end portion 604 of the conductor 524a is extended through the first conductor aperture 420a and into the contact assembly lumen (502 in FIG. 5A). The first conductor 524a is passed through the first conductor aperture 420a, and out the first end portion 404 of the contact assembly 402. In at least some embodiments, the terminal 432a is slid over the contact assembly 402 from the second end portion 406 of the contact assembly 402 until it reaches the first annular groove 412a.

The second end portion 604 of the conductor 524a is extended out of the first end portion 404 of the contact assembly 402. To enable the first terminal 432a to slide along the contact assembly 402, at least a portion of the contact assembly 402 is compressible to enable portions of the contact assembly 402 to fit within a bore of the first terminal 432a. Thus, in preferred embodiments, since the contacts are themselves not compressible, the contacts are disposed on the contact assembly 402 from the second end portion 406 of the contact assembly 402 towards the first end portion 404 of the contact assembly 402.

Once the first conductor 524a is extended through the first conductor aperture 420 and out the first end portion 406 of the contact assembly 402, the first conductor 524a can be extended along the lead body 452 and coupled to the electrodes 472. Similarly, each of the terminals 432 may be placed within the designated annular grooves 412 from the second end portion 406 to the first end portion 404 of the contact assembly 402. After disposing all the terminals 432 over the contact assembly 402, the first end portion 404 of the contact assembly 402 is coupled to proximal end 454 of the lead body 452.

FIG. 6B is a schematic side view of one embodiment of the first terminal 432a disposed in the first annual groove 420a and the second terminal 432b configured and arranged for disposing in the second annual groove 420b. A first end 612 of an elongated second conductor 524b is coupled to second terminal 432b. An opposing end 614 of the second conductor 524b is extended into the second conductor aperture 420b defined in the second annular groove 412b of the contact assembly 402. The second conductor 524b is extended through the second conductor aperture 420b and the terminal 432b is slid over the contact assembly 402 until being disposed in the second annular groove 412b. The second end 614 of the conductor 524b is extended out of the first end portion 404 of the contact assembly 402.

Turning to FIG. 6C, the second ends of the conductors 524 that extend from the first end portion 404 of the contact assembly 402 may be extended along the lead body 452 and electrically coupled to the electrodes 472. FIG. 6C is a schematic side view of one embodiment of the contact assembly 402, the terminals 432, the lead body 452, and the electrodes 472. As shown in FIG. 6C, the terminals 432 are coupled to the contact assembly 402, in particular, each terminal 432 is disposed within a corresponding annular groove 412. The conductors 524 are electrically coupled to each terminal 432 and are extended along the lead body 452 and electrically coupled to the electrodes 472.

Once the terminals 432 are each disposed over the contact assembly 402, a stiffening agent (e.g., an epoxy) may be used to reduce the compressibility of the contact assembly 402. In at least some embodiments, the stiffening agent is applied to the contact assembly lumen 502 (see e.g., FIG. 5B). In at least some embodiments, the stiffening agent is infused into the mesh of the contact assembly 402 to form a matrix.

In at least some embodiments, the terminals 432 are mechanically coupled to the annular grooves 412 using various attachment methods including, for example, re-flowing, one or more adhesives, compression fitting, or the like. In at least some embodiments, the number of conductors 524 are equal to number of electrodes or terminals 432. Typically, each terminal 432 is electrically coupled to one electrode 472. In at least some embodiments, each terminal 432 is coupled to more than one electrode 472. In at least some embodiments, the number of terminals 432 is no fewer than the number of electrodes 472.

The contact assembly 402 may be coupled to the distal end portion 454 of the lead body 452 in any suitable manner including, for example, re-flowing, one or more adhesives, or the like. It may be an advantage to re-flow the material of the contact assembly 402, or the lead body 452, or both, to couple the contact assembly 402 to the lead body 452 in a strong and cohesive manner. In at least some embodiments, the terminals 432, the contact assembly 402, or both may be ground down to ensure that the terminals 432, the contact assembly 402, and the lead body 452 are isodiametric.

FIGS. 4A-6C illustrate one embodiment of disposing terminals on a contact assembly and coupling the contact assembly to a proximal end portion of a lead body. As shown in FIGS. 7A-7B, in at least some embodiments contact assemblies can, alternately, be formed for receiving electrodes and for being coupled to distal end portions of the lead body.

FIG. 7A is a schematic side view of one embodiment of a contact assembly 702 configured and arranged for coupling to the distal end portion 456 of the lead body 452. FIG. 7B is a schematic side view of one embodiment of a lead 700 that includes the electrodes 472 coupled to the contact assembly 702, and the contact assembly 702 coupled to the distal end portion 456 of the lead body 452.

The contact assembly 702 includes a first end portion 704, a second end portion 706, and an outer surface 708. A plurality of annular grooves 712 are defined along the outer surface 708. The annular grooves 712 further include a first annular groove 712a and a second annular groove 712b. Conductor apertures 720 are defined in each of the annular grooves 712. The electrodes 472 are disposed in the annular grooves 712, with a first electrode 472a disposed in the first annular groove 712a and a second electrode 472b disposed in the second annular groove 712b. Conductors (not shown) electrically couple the electrode 472 to the terminals 432.

Figure 8:
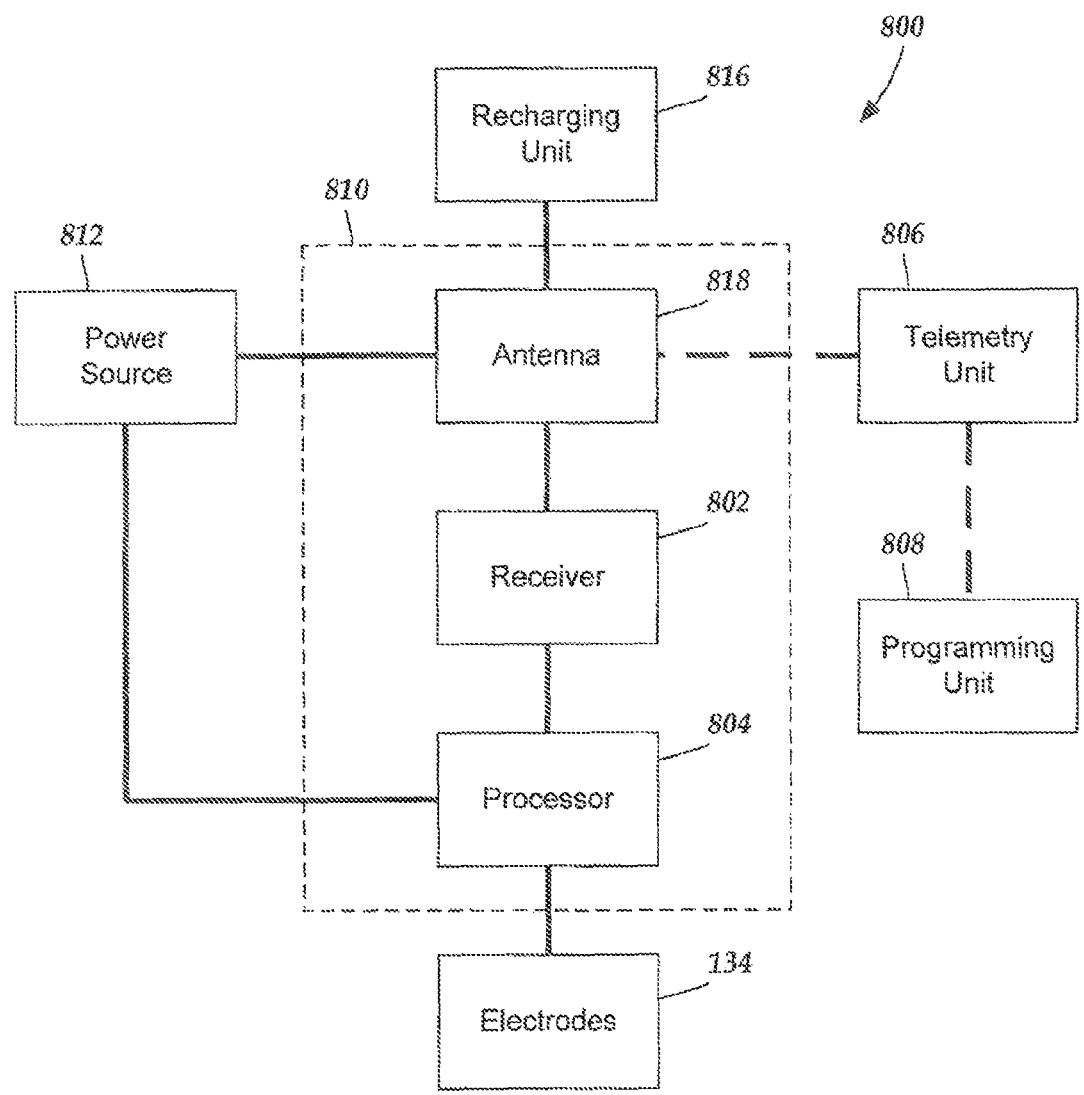
FIG. 8 is a schematic overview of one embodiment of components of a stimulation system, including an electronic subassembly disposed within a control module, according to the invention.

FIG. 8 is a schematic overview of one embodiment of components of an electrical stimulation system 800 including an electronic subassembly 810 disposed within a control module. It will be understood that the electrical stimulation system can include more, fewer, or different components and can have a variety of different configurations including those configurations disclosed in the stimulator references cited herein.

Some of the components (for example, a power source 812, an antenna 818, a receiver 802, and a processor 804) of the electrical stimulation system can be positioned on one or more circuit boards or similar carriers within a sealed housing of an implantable pulse generator, if desired. Any power source 812 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 818 or a secondary antenna. The external power source can be in a device that is mounted on the skin of the user or in a unit that is provided near the user on a permanent or periodic basis.

If the power source 812 is a rechargeable battery, the battery may be recharged using the optional antenna 818, if desired. Power can be provided to the battery for recharging by inductively coupling the battery through the antenna to a recharging unit 816 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 804 is generally included to control the timing and electrical characteristics of the electrical stimulation system. For example, the processor 804 can, if desired, control one or more of the timing, frequency, strength, duration, and waveform of the pulses. In addition, the processor 804 can select which electrodes can be used to provide stimulation, if desired. In some embodiments, the processor 804 selects which electrode(s) are cathodes and which electrode(s) are anodes. In some embodiments, the processor 804 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 808 that, for example, allows modification of pulse characteristics. In the illustrated embodiment, the processor 804 is coupled to a receiver 802 which, in turn, is coupled to the optional antenna 818. This allows the processor 804 to receive instructions from an external source to, for example, direct the pulse characteristics and the selection of electrodes, if desired.

In one embodiment, the antenna 818 is capable of receiving signals (e.g., RF signals) from an external telemetry unit 806 which is programmed by the programming unit 808. The programming unit 808 can be external to, or part of, the telemetry unit 806. The telemetry unit 806 can be a device that is worn on the skin of the user or can be carried by the user and can have a form similar to a pager, cellular phone, or remote control, if desired. As another alternative, the telemetry unit 806 may not be worn or carried by the user but may only be available at a home station or at a clinician's office. The programming unit 808 can be any unit that can provide information to the telemetry unit 806 for transmission to the electrical stimulation system 800. The programming unit 808 can be part of the telemetry unit 806 or can provide signals or information to the telemetry unit 806 via a wireless or wired connection. One example of a suitable programming unit is a computer operated by the user or clinician to send signals to the telemetry unit 806.

The signals sent to the processor 804 via the antenna 818 and the receiver 802 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 800 to cease operation, to start operation, to start charging the battery, or to stop charging the battery. In other embodiments, the stimulation system does not include the antenna 818 or receiver 802 and the processor 804 operates as programmed.

Optionally, the electrical stimulation system 800 may include a transmitter (not shown) coupled to the processor 804 and the antenna 818 for transmitting signals back to the telemetry unit 806 or another unit capable of receiving the signals. For example, the electrical stimulation system 800 may transmit signals indicating whether the electrical stimulation system 800 is operating properly or not or indicating when the battery needs to be charged or the level of charge remaining in the battery. The processor 804 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation lead, comprising:
   a lead body having a distal end portion, a proximal end portion, and a longitudinal length;
   a plurality of electrodes disposed along the distal end portion of the lead body;
   a plurality of terminals disposed along the proximal end portion of the lead body;
   a plurality of conductors, each conductor of the plurality of conductors electrically coupling each of the plurality of terminals to at least one of the plurality of electrodes; and
   a contact assembly formed from a shaped mesh, the contact assembly disposed at one of the proximal end portion or the distal end portion of the lead body, the shaped mesh having an outer surface and defining a contact assembly lumen, the shaped mesh comprising
      a plurality of annular grooves defined along the outer surface of the shaped mesh, and
      at least one conductor aperture defined in each of the plurality of annular grooves, the at least one conductor aperture extending between the outer surface and the contact assembly lumen,
      wherein each of the plurality of conductors extends through the at least one conductor aperture and along at least a portion of the shaped mesh within the contact assembly lumen,
      wherein for each annular groove of the plurality of annular grooves, one of the plurality of electrodes or one of the plurality of terminals is disposed in the annular groove.

2. The electrical stimulation lead of claim 1, further comprising a stylet tube disposed within the contact assembly lumen, wherein the stylet tube defines a stylet lumen, and wherein each of the plurality of conductors extends through the at least one conductor aperture and along at least a portion of the shaped mesh within the contact assembly lumen and external to the stylet tube.

3. The electrical stimulation lead of claim 1, further comprising a stiffening agent infused into the shaped mesh to form a matrix with the shaped mesh.

4. The electrical stimulation lead of claim 3, wherein the stiffening agent is an epoxy.

5. The electrical stimulation lead of claim 3, wherein the stiffening agent is disposed in the contact assembly lumen.

6. A method of forming an electrical stimulation lead, the method comprising:
   providing a contact assembly formed from a shaped mesh, the contact assembly having a first end portion, a second end portion, a longitudinal length, and an outer surface, wherein the contact assembly comprises a plurality of annular grooves defined along the outer surface of the shaped mesh, the plurality of annular grooves comprising a first annular groove and a second annular groove, wherein a first conductor aperture is defined within the first annular groove, and wherein a second conductor aperture is defined within the second annular groove;
   coupling a first end portion of an elongated first conductor to a first contact;
   extending a second end portion of the first conductor through the first conductor aperture of the contact assembly;
   disposing the first contact within the first annular groove;
   extending the second end portion of the first conductor out of the first end portion of the contact assembly;
   extending the second end portion of the first conductor into a first end portion of a lead body;
   coupling the second end portion of the first conductor to a second contact disposed along a second end portion of the lead body; and
   coupling the first end portion of the lead body to the first end portion of the contact assembly.

7. The method of claim 6, further comprising
   coupling a first end portion of an elongated second conductor to a third contact;
   extending a second end portion of the second conductor through the second conductor aperture of the contact assembly;
   disposing the third contact within the second annular groove;
   extending the second end portion of the second conductor out of the first end portion of the contact assembly;
   extending the second end portion of the second conductor into a first end portion of a lead body; and
   coupling the second end portion of the second conductor to a fourth contact disposed along the second end portion of the lead body.

8. The method of claim 6, wherein providing a contact assembly formed from a shaped mesh comprises providing a contact assembly formed from a shaped mesh that comprises polyethylene terephthalate.

9. The method of claim 6, wherein providing a contact assembly comprises providing a contact assembly that comprises a contact assembly lumen defined in the shaped mesh, the contact assembly lumen extending along the entire longitudinal length of the contact assembly, and wherein the first and second conductors extend along at least a portion of the contact assembly lumen.

10. The method of claim 9, wherein disposing the first contact within the first annular groove comprises compressing at least a portion of the shaped mesh to enable the first contact to slide along the contact assembly.

11. The method of claim 9, wherein disposing the first contact within the first annular groove comprises disposing a ring-shaped contact within the first annular groove.

12. The method of claim 9, wherein providing a contact assembly comprises providing a contact assembly that comprises a stylet tubing disposed in the contact assembly lumen, wherein the stylet tubing defines a stylet lumen configured and arranged for receiving a stylet, and wherein the first and second conductors extend along at least a portion of the contact assembly lumen external to the stylet tubing.

13. The method of claim 12, further comprising applying a stiffening agent to the contact assembly lumen after disposing the first contact within the first annular groove.

14. The method of claim 13, wherein applying a stiffening agent to the contact assembly lumen comprises infusing the stiffening agent into the shaped mesh to form a matrix with the shaped mesh.

15. The method of claim 13, wherein applying a stiffening agent to the contact assembly lumen applying an epoxy to the contact assembly lumen.

16. The method of claim 6, wherein coupling a first end portion of an elongated first conductor to a first contact comprises coupling the first end portion of the first conductor to an electrode.

17. The method of claim 6, wherein coupling a first end portion of an elongated first conductor to a first contact comprises coupling the first end portion of the first conductor to a terminal.

18. The method of claim 6, further comprising disposing a retention sleeve within a retention sleeve annular groove defined along the outer surface of the shaped mesh.

19. The method of claim 6, wherein coupling the first end portion of the lead body to the first end portion of the contact assembly comprises reflowing at least one of a material forming the contact assembly or a material forming the lead body to couple the first end portion of the lead body to the first end portion of the contact assembly.

20. A method of forming an electrical stimulation lead, the method comprising:

providing a contact assembly, the contact assembly having a first end portion, a second end portion, a longitudinal length, and an outer surface, wherein the contact assembly comprises a plurality of annular grooves defined along the outer surface of the contact assembly, the plurality of annular grooves comprising a first annular groove and a second annular groove, wherein a first conductor aperture is defined within the first annular groove, and wherein a second conductor aperture is defined within the second annular groove;

coupling a first end portion of an elongated first conductor to a first contact;

extending a second end portion of the first conductor through the first conductor aperture of the contact assembly;

disposing the first contact within the first annular groove;

extending the second end portion of the first conductor out of the first end portion of the contact assembly;

extending the second end portion of the first conductor into a first end portion of a lead body;

coupling the second end portion of the first conductor to a second contact disposed along a second end portion of the lead body; and coupling the first end portion of the lead body to the first end portion of the contact assembly.

* * * * *